United States Patent [19]

Studt et al.

[11] Patent Number: 4,906,630

[45] Date of Patent: Mar. 6, 1990

[54] METHOD OF INCREASING CARDIAC CONTRACTILITY USING PHARMACEUTICAL COMPOSITIONS COMPRISING BENZODIAZINONE-PYRIDAZINONE OR HYDROXY-PYRAZOLYL COMPOUNDS

[75] Inventors: William L. Studt, Harleysville; William C. Faith, Ambler; Bruce F. Molino, Lansdale, all of Pa.

[73] Assignee: Rorer Pharmaceutical Corporation, Fort Washington, Pa.

[21] Appl. No.: 255,664

[22] Filed: Oct. 11, 1988

Related U.S. Application Data

[62] Division of Ser. No. 63,481, Jun. 17, 1987, Pat. No. 4,785,101, which is a division of Ser. No. 800,986, Nov. 22, 1985, Pat. No. 4,725,686.

[51] Int. Cl.$^4$ .................. A61K 31/50; A61K 31/415
[52] U.S. Cl. .................. 514/254; 514/213; 514/249; 514/259; 514/387; 540/543; 540/567; 540/570; 540/493; 540/495; 540/500; 544/119; 544/230; 544/231; 544/235; 544/237; 544/238; 544/249; 544/284; 544/354; 548/305
[58] Field of Search ............... 514/254, 213, 249, 259, 514/387

[56] References Cited

U.S. PATENT DOCUMENTS

| | | | |
|---|---|---|---|
| 4,026,891 | 5/1977 | Austel et al. | 544/114 |
| 4,361,563 | 11/1982 | Austel et al. | 544/238 |
| 4,644,000 | 2/1987 | Gauss et al. | 544/284 |
| 4,666,913 | 5/1987 | Kubla et al. | 544/284 |

*Primary Examiner*—Glennon H. Hollrah
*Assistant Examiner*—James H. Turnipseed
*Attorney, Agent, or Firm*—Martin F. Savitzky; James A. Nicholson; Alexis Barron

[57] ABSTRACT

A method for increasing cardiotonic contractility in humans or other animals using a class of benzodiazinone-pyridazinone and hydroxy-pyrazolyl compounds and pharmaceutical compositions including the same.

18 Claims, No Drawings

METHOD OF INCREASING CARDIAC CONTRACTILITY USING PHARMACEUTICAL COMPOSITIONS COMPRISING BENZODIAZINONE- PYRIDAZINONE OR HYDROXY-PYRAZOLYL COMPOUNDS

This is a division of co-pending application Ser. No. 063,481, filed on Jun. 17, 1987, now U.S. Pat. No. 4,785,101, which is a division of application Ser. No. 800,986, filed on Nov. 22, 1985, now U.S. Pat. No. 4,725,686.

FIELD OF THE INVENTION

This invention relates to substituted benzodiazinones useful as cardiotonic agents for the treatment of congestive heart failure. This invention also relates to methods for increasing cardiac contractility using said compounds, and pharmaceutical compositions including said compounds.

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Inotropic drugs include the 5-pyridyl substituted pyridones disclosed in U.S. Pat. Nos.: 4,004,012; 4,072,746; 4,107,315; 4,137,233; 4,199,586; 4,271,168; and 4,107,315; in GB No. 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572 and the 5-phenyl-thiazole compounds disclosed in U.S. Pat. No. 4,418,070.

Cardiotonic bicyclic heteroaryl-5-substituted pyridyl compounds are disclosed in U.S. Ser. No. 410,646, and cardiotonic diazaheterocyclic-5-substituted pyridyl compounds are disclosed in U.S. Pat. No. 4,432,979 and U.S. Ser. Nos. 314,692 and 493,336, all of which are assigned to the same assignee as the present application.

Cardiotonic 4,5-dihydro-5-[4-(H-imidazol-1-yl)phenyl]-3(2H)-pyridazinones are disclosed in Bristol et al., J. Med. Chem. 22, 1099 (1984); cardiotonic imidazolyl substituted pyridazinones are disclosed in U.S. Pat. No. 4,521,416, and cardiotonic benzothiazolone substituted pyridazinones are disclosed in published EPO patent application Ser. No. 84108656.4 (Publ. No. 0132817). Cardiotonic compounds including a pyrazole group are disclosed in published EPO patent application Ser. No. 84303456.2 (Publ. No. 0126651) and U.S. Pat. Nos. 4,526,895 and 4,526,982.

SUMMARY OF THE INVENTION

The present invention relates to a method for increasing cardiac contractility in humans and other mammals comprising the administration of an effective inotropic amount of a heterocyclic substituted benzodiazinone compound.

The preferred method comprises the administration of benzodiazinone compounds substituted by either a pyridazinone or hydroxy pyrazolyl ring.

This invention comprises particularly the administration to a patient of an effective inotropic amount of a benzodiazinone compound within the scope by Formula I:

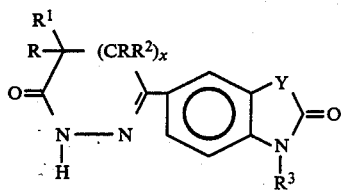

wherein:
x is 0 or 1;
Y is

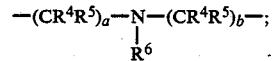

a and b are 0, 1 or 2, provided that a+b is not greater than 2;
$R^1$, $R^2$, $R^3$, $R^4$ and $R^6$ are each independently H, alkyl or aralkyl;
R and $R^5$ are H or alkyl;
R or $R^5$ groups on vicinal carbon atoms may together form a carbon-carbon double bond; and
geminal $R^4$ and $R^5$ groups may together form a spiro substituent, —$(CH_2)_d$—, where d is 2 to 5;
or a pharmaceutically acceptable salt thereof.

This invention also relates to compounds of Formula I, provided that when a=b=0 and x=1, then at least one of R, $R^1$, $R^2$, $R^3$ or $R^6$ is other than hydrogen, and pharmaceutical compositions which comprise compounds of Formula I and which are effective in increasing cardiac contractility in humans.

DETAILED DESCRIPTION

Certain of the compounds encompassed within the present invention, and particularly, compounds of Formula I, may exist in enolic or tautomeric forms, and all of these forms are considered to be included within the scope of this invention.

The compounds of this invention which have particular usefulness as cardiotonic agents are described by Formula I wherein the benzodiazinone ring is described by one of Formulae

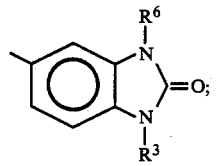

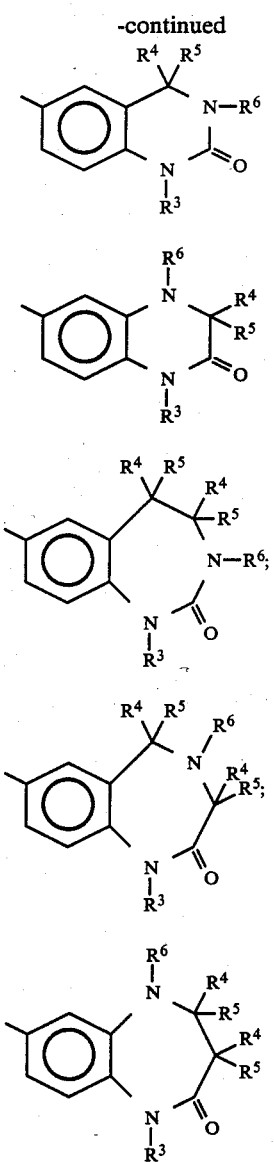

wherein:

R³, R⁴, R⁵ and R⁶ are as described above.

A most preferred class of compounds within the present invention includes compounds of Formulae I, II, IIIa and IVa wherein at least one of R, R¹, R², R³, R⁴, R⁵ or R⁶ is other than hydrogen.

More preferred compounds are those disclosed by Formula I, wherein:

either R³ or R⁴ or R⁶ is lower alkyl.

A special embodiment of the present invention comprises compounds of Formula I where R⁴ and R⁵ form a spiro ring system, an example of which is shown by Formula V:

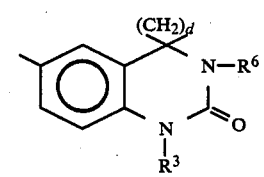

Other preferred embodiments include those compounds according to Formula I wherein:

x is 1; and

R and R form a double bond.

As employed above and throughout the disclosure, the following terms, unless otherwise indicated, shall be understood to have the following meanings:

"Alkyl" means a saturated aliphatic hydrocarbon which may be either straight- or branched-chained containing from about one to about 6 carbon atoms.

"Lower alkyl" means an alkyl group as above, having 1 to about 4 carbon atoms.

"Aryl" means an aromatic hydrocarbon radical. The preferred aryl groups are phenyl and substituted phenyl.

"Aralkyl" means an alkyl group substituted by an aryl radical. The preferred aralkyl groups are lower alkyl groups substituted by phenyl or substituted phenyl.

"Substituted phenyl" means a phenyl group substituted by one or more of lower alkyl, lower alkoxy, amino, lower alkyl amino, lower alkyl mercapto, hydroxy, hydroxy lower alkyl, acetoxy, benzyloxy, phenoxy, lower alkyl sulfinyl or lower alkyl sulfonyl.

"Hydroxy alkyl" means an alkyl group substituted by a hydroxy group. Hydroxy lower alkyl groups are preferred and include hydroxymethyl, 2-hydroxyethyl, 2-hydroxypropyl, and 3-hydroxypropyl.

"Alkoxy" means an alkyl oxy radical group. Lower alkoxy groups are preferred and include methoxy, ethoxy, n-propoxy, i-propoxy, sec-propoxy, n-butoxyl among others.

"Alkyl mercapto" means a radical of the formula —S—R where R is alkyl. Lower alkyl mercapto groups are preferred.

"Alkylsulfinyl" means a R—SO— radical where R is alkyl.

"Alkylsulfonyl" means a R—SO₂— radical where R is alkyl. Lower alkyl sulfonyl groups are preferred.

"Amino" means —NH₂ and "alkyl amino" means —NHR where R is alkyl. Lower alkyl amino groups are preferred.

The compounds of this invention may be useful in the form of the free base, if a basic group is present, in the form of salts and as a hydrate, and all forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds within the scope of Formula I may be prepared in accordance with the following reaction sequences.

-continued
Scheme I

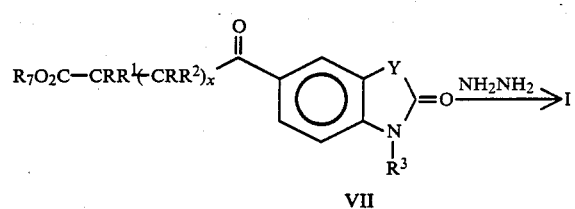

When R is H and x is 1 in Formula I above, the 3,4-dihydro-pyridazinone compounds may be converted to their aromatic derivatives by treating the dihydro compound with bromine in acetic acid. An alternate method comprises the use of an unsaturated maleic acyl halide derivative as the Friedel Crafts reagent shown in Scheme II below. See W. V. Curran, A. Ross, *J. Med. Chem.*, 17, 273 (1974).

Scheme II

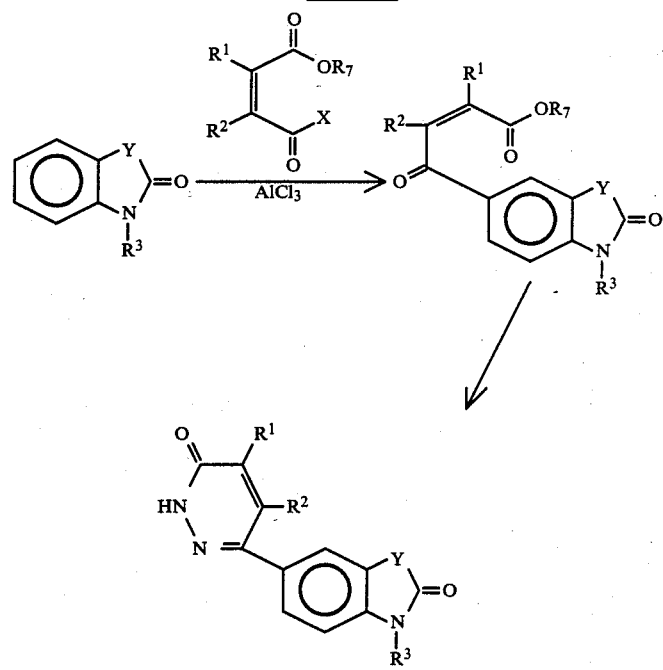

Treatment of a benzodiazinone intermediate VI (when a≠0) with an acyl halide under Friedel-Crafts reaction conditions forms the acylation adduct VII. Ring closure to afford the compounds of Formula I is accomplished with hydrazine. See Scheme I below.

Scheme I

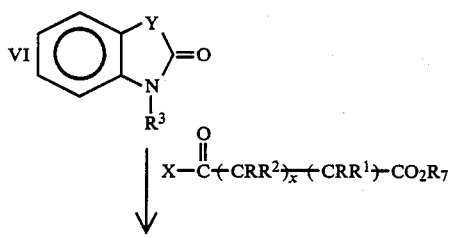

The benzodiazinone intermediates VI, particularly the unsubstituted and lower alkyl substituted compounds, are either known compounds or may be prepared in accordance with the reaction sequences described below.

The 3,4-dihydro-2(1H)-quinazolinone intermediates may be prepared from analogous 2-carbamoyl anilines by reducing the carbamoyl functionality to the methylene amine. Treatment of the resulting diamine with carbonyldiimidazole in THF affords the 3,4-dihydro-2(1H)-quinazolinone. See Scheme III below.

Scheme III

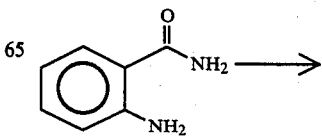

-continued
Scheme III

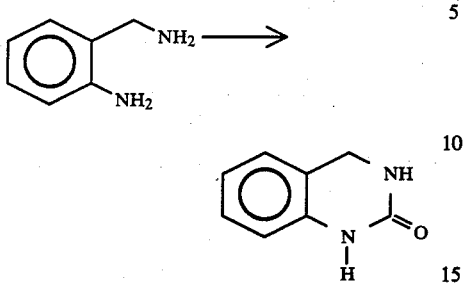

When b=0, a=1 and at least one of $R^4$ or $R^5$ is hydrogen in Formula I above and $R^3$ is as described above, the intermediate quinazolinone may be prepared as shown in Scheme IV below.

Scheme IV

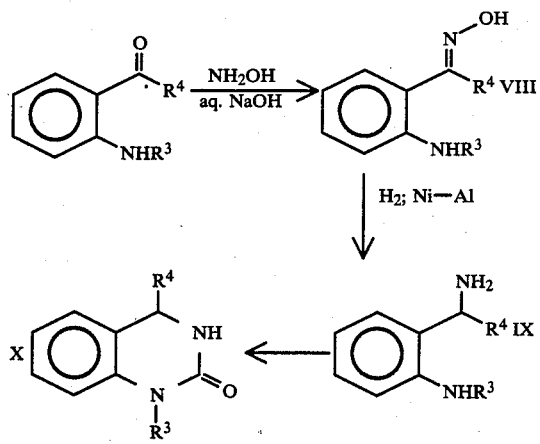

Treatment of 1-$R^4$-(2-$R^3$-substituted aniline)-ketone with hydroxylamine and aqueous sodium hydroxide affords the oxime, VIII. Catalytic hydrogenation, preferably using Al-Ni catalyst, results in the amine IX, which may be cyclized, using carbonyldiimidazole, to the $R^4$-substituted-2(1H)-quinazolinone. When $R^3$ is hydrogen in Scheme IV above, the $R^4$ substituted intermediate, X, may be alkylated selectively in the $R^3$ position using a hydride reagent in a polar aprotic solvent and an appropriate alkylating reagent, preferably sodium hydride in DMSO.

The preparation of $R^6$-substituted benzodiazinone intermediates is shown in Scheme V below.

Scheme V

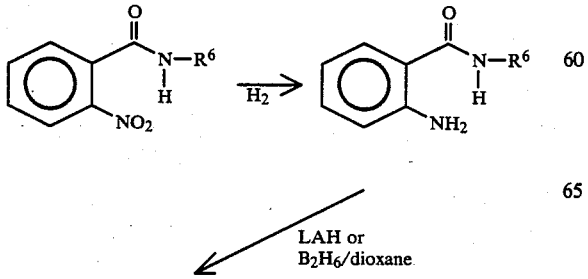

-continued
Scheme V

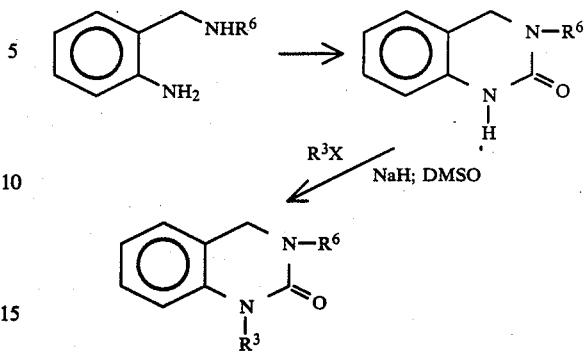

Catalytic hydrogenation of a $R^6$-substituted-2-nitrobenzamide followed by the hydride reduction of the $R^6$-substituted-2-amino-benzamide results in the methylene diamine which may be cyclized to the $R^6$-substituted-2(1H)-quinazolinone. See, M. R. Boots, S. G. Boots, J. Med. Chem., 13, 144 (1969). Alkylation of the 1-N position affording $R^3$-substitution may be accomplished at this stage. See, W. E. Coyne and J. W. Cusic, infra. Another method for the preparation of the $R^6$ substituted quinazolinone intermediates involves the rearrangement of a quinazolidinol as reported in Pilicheva, et al., Dokl. Akad. Nauk SSSR 1974, 218(6), 1375-6.

Another method for the preparation of $R^3$-substituted 2H-quinazolinones is described by W. E. Coyne and J. W. Cusic, J. Med. Chem., 11, 1208 (1968), hereby incorporated by reference. Treatment of a 1-N-substituted isatoic anhydride with ammonia affords the 2-substituted amino benzamide, which may be reduced to the diamine and cyclized to the 1-N-substituted intermediate as described above. The 3-position may be alkylated to give the 1-$R^3$, 3-$R^6$-disubstituted intermediate compounds.

The spiro compounds of Formula I, wherein $R^4$ and $R^5$ together are —$(CH_2)_d$—, may be prepared from the 2-nitro styryl intermediate, XI, shown in Scheme VI below.

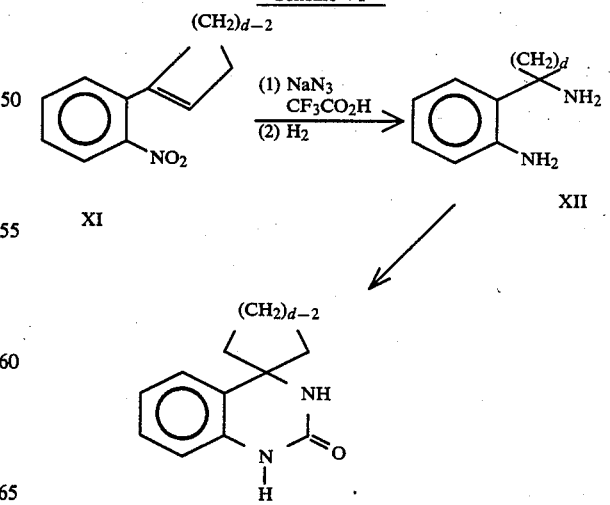

Treatment of the styryl intermediate with sodium azide in trifluoroacetic acid, followed by the reduction of the nitro and azido groups results in the diamine intermediate, XII. Cyclization with carbonyl diimidazole results in the spiro benzodiazinone intermediate.

The spiro compounds may also be derived from the 2-amino styryl intermediate, which may be prepared from aniline according to Scheme VII below.

cyclization temperatures, about 100° to about 200° C., preferably in an aprotic polar solvent, for about 15 min. to about two days.

The 7-membered benzodiazepinone compounds of Formula I may be prepared according to Scheme VIII below.

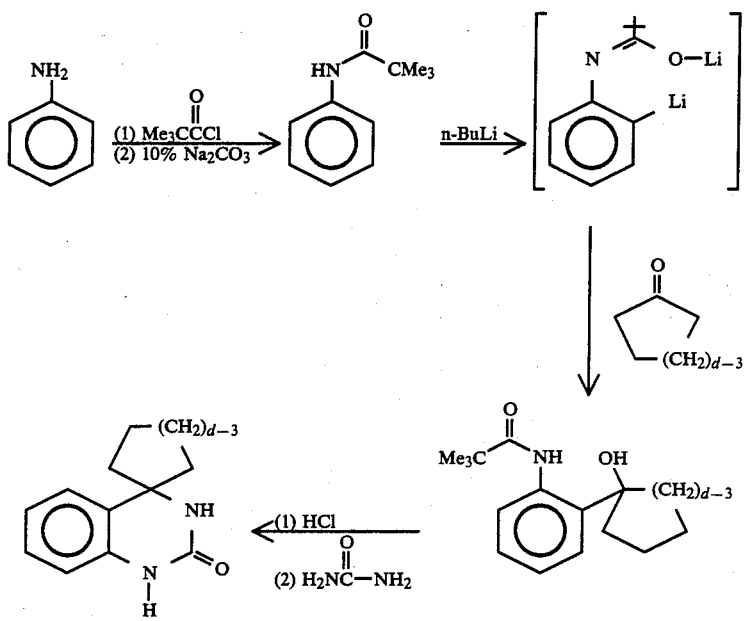

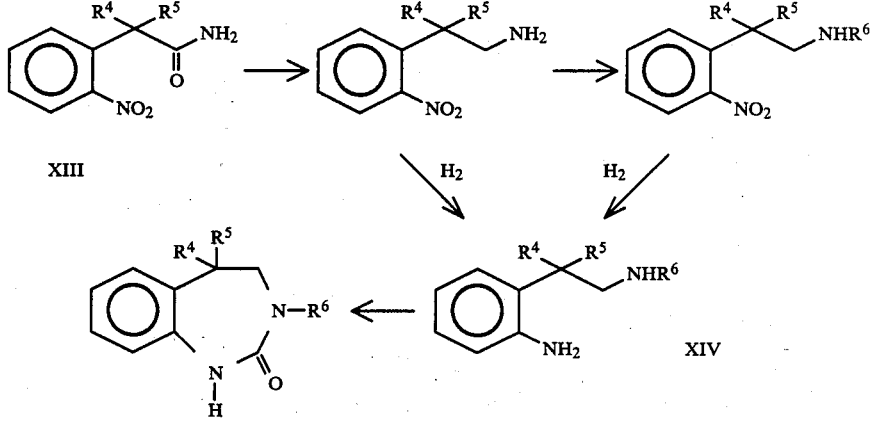

Treatment of aniline with a trialkylacetyl chloride, such as trimethylacetyl chloride, followed by neutralization with 10% aqueous alkali metal carbonate, results in the trialkyl acetamide. Treatment of the amide with n-butyl lithium forms the metallated intermediate, shown above, which is reacted with a carbocyclic ketone, thereby forming the tertiary alcohol intermediate. See, H. Gschwend, W. Fuhrer, *J. Org. Chem.* 44, 1133, 1979. The alcohol may be dehydrated and the amine deprotected in one step by acid hydrolysis using, for example, aqueous hydrochloric acid. Cyclization to the spiro benzodiazinone intermediate may be accomplished by heating a neat mixture of the amine and urea to about 100° to about 200° C. See, L. Bernardi et al., *Ger. Offen.* 1,958,515 (1970), hereby incorporated by reference. Alternatively, the mixture may be heated to Reduction of the 2-nitrobenzylamide XIII with diborane followed by the catalytic hydrogenation of the nitro group affords the diamine intermediate, XIV. Treatment of the diamine intermediate with carbonyldiimidazole results in the benzodiazepinone intermediate. Either the diamine intermediate, XIV, or the benzodiazepinone intermediate may be alkylated, affording the 1- and/or 3-substituted benzodiazepinone compounds.

When a=0 in Formula I above, the compounds of this invention may be prepared from the formyl-substituted N-acetyl intermediate XV, shown in Scheme IX, below.

Scheme IX

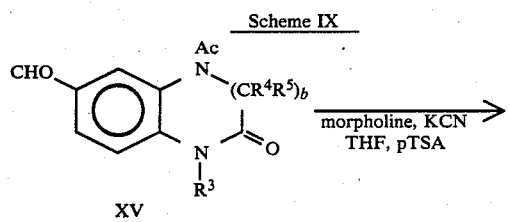

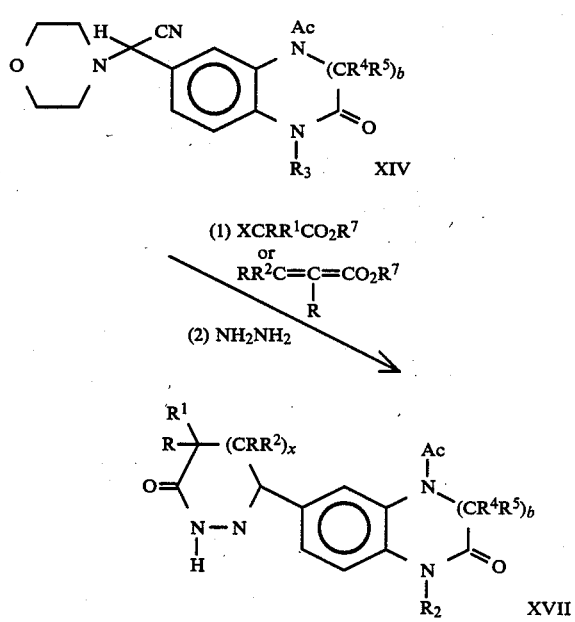

Treatment of intermediate XV with p-toluene sulfonic acid, morpholine and potassium cyanide in refluxing THF results in the cyano morpholino intermediate XVI. Treatment of the morpholino intermediate XVI with a strong base, such as lithium diisopropylamide in THF, sodium methoxide in THF or sodium hydride in DMF, and a halo acetic acid or an alpha, beta unsaturated carboxylic acid (or alkyl esters thereof) results in the formation of the alkylation or 1,4-addition product ($R^7$ is H or lower alkyl in Scheme IX above). Treatment of the alkylation or addition product with hydrazine results in the cyclized intermediate XVII. The N-acetyl group on intermediate XVII may be hydrolyzed with acid and one or both of the nitrogen atoms in the ring alkylated if desired.

The formyl-intermediate XV may be prepared from the commercially available 4-nitro-1,2-phenylenediamine as shown in Scheme X, below.

Scheme X

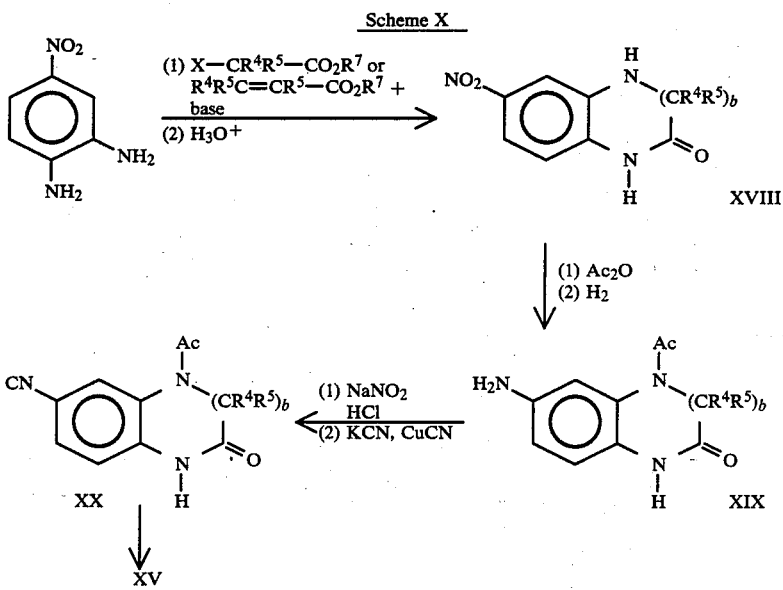

The nitro-substituted bicyclic intermediate XVIII may be prepared by the N-alkylation of the diamine with an alpha, beta unsaturated carboxylic acid (or alkyl ester) or halo acetic acid (or alkyl ester), such as bromo acetic acid, followed by acid or base treatment to the bicyclic intermediate. For example, when the phenylenediamine is reacted with acrylic acid under acidic conditions, 7-nitro-1,3,4,5-tetrahydro-1,1-1,5-benzodiazepine-2-one is formed. See, G. A. Archer & L. H. Sternbach, Chem. Rev. 68, 747–784, 1968; and G. B. Bachman & L. V. Heisey, J. Am. Chem. Soc. 71, 1985, 1949. Treatment of the cyclic amine XVIII with acetic anhydride in the presence of a non-nucleophilic base such as triethylamine, followed by catalytic hydrogenation under standard hydrogenation conditions such as hydrogen gas (55 psi) over 5% palladium on carbon in methanol, results in the reduction of the nitro group to the amine, XIX.

The aldehyde intermediate XV may be prepared by converting the amine to the diazonium salt by treatment with a nitrite salt, such as sodium nitrite, under acidic conditions. The diazonium intermediate may be converted to the nitrile group by treatment with a mixture of copper cyanide and potassium cyanide. See, W. V. Curran & A. Ross, J. Med. Chem. 17, 273, 1974. The nitrile intermediate XX may be selectively reduced the aldehyde using a hydride reagent, such as diisobutyl aluminum hydride. See, A. E. G. Miller, S. W. Biss, L. H. Schwartzman, J. Org. Chem. 24, 627, 1959.

Examples of the preparation of compounds within the scope of the present invention are presented below.

EXAMPLE 1

The Preparation of
3,4-Dihydro-6-[3-(4,5-Dihydropyridizin-6-one)]-2(1H)-Quinazolinone

Step 1.
6-(3-Carboxy-propionyl)-3,4-dihydro-2(1H)-quinazolinone 3,4-Dihydro-2(1H)-quinazolinone (4.8 g) is added to a stirred suspension of anhydrous aluminum chloride (21.7 g) in carbon disulfide (100 ml) under nitrogen. Methyl succinyl chloride (4.9 g) is added dropwise to the stirred suspension, the reaction mixture refluxed for about 70 hours, cooled to RT and the liquid phase decanted. The residue is treated with ice and 6N HCl, filtered, and the solid air dried, affording the desired crude product, M.P. 176°–180° C., which is used in the next step without further purification.

Step 2.
3,4-Dihydro-6-[3-(4,5-dihydro-pyridizin-6-one)]-2(1H)-quinazolinone

Hydrazine monohydrate (0.24 g) is added to a stirred mixture of the keto acid obtained in Step 1. (1 g) in absolute ethanol (25 ml). The reaction mixture is refluxed for about 20 hours, cooled to RT, filtered, the filtered solid washed with absolute ethanol and dried, affording the desired product, M.P.>250° C.

EXAMPLE 2

The Preparation of
3,4-Dihydro-6-[5-(3-Hydroxypyrazolyl)]-2(1H)-Quinazolinone

Step 1.
6-(2-Carboethoxy)-3,4-dihydro-2(1H)-quinazolinone 3,4-Dihydro-2(1H)-quinazolinone (4.8 g) is added to a stirred suspension of anhydrous aluminum chloride (21.7 g) in carbon disulfide (100 ml) under nitrogen. Ethyl malonyl chloride (4.9 g) is added dropwise to the stirred suspension. The reaction mixture is refluxed for about 70 hours, cooled to RT and the liquid phase decanted. The residue is treated with ice and 6N HCl, filtered, and the solid air dried, affording the desired crude product, which is used in the next step without further purification.

Step 2.
3,4-Dihydro-6-[5-(3-hydroxypyrazolyl)]-2(1H)-quinazolinone

Hydrazine monohydrate (0.24 g) is added to a stirred mixture of the keto acid obtained in Step 1. above (1 g) in absolute ethanol (25 ml). The reaction mixture is refluxed for about 20 hours, cooled to RT, filtered to a tan solid, which is washed with absolute ethanol and dried, affording the desired product.

EXAMPLE 3

The Preparation of
3,4-Dihydro-6-[3-(4,5-Dihydro-4-Methyl-Pyridizin-6-one)]-2(1H)-Quinazolinone

Step 1.
6-(3-Carbomethoxy-2-methyl-propionyl)-3,4-dihydro-2(1H)-quinazolinone 3,4-Dihydro-2(1H)-quinazolinone (3.6 g) is added to a stirred suspension of anhydrous aluminum chloride (16.5 g) in carbon disulfide (120 ml) under nitrogen. 3-Carbomethoxy-2-methyl-propionyl chloride (4 g) is added dropwise to the stirred suspension, and the reaction mixture refluxed for about 18 hours, cooled to RT and further cooled to 0° C. in an ice bath. The liquid phase is decanted and ice and cold water slowly added to the residue. The aqueous mixture is filtered and the filtered solid suspended and stirred in the anhydrous diethyl ether overnight. The suspension is filtered and the filtered solid used in the next step without further purification.

Step 2.
3,4-Dihydro-6-[3-(4,5-dihydro-4-methyl-pyridizin-6-one)]-2(1H)-quinazolinone Hydrazine monohydrate (1.1 g) is added to a stirred suspension of the keto ester obtained in Step 1. above (4.9 g) in absolute ethanol (100 ml). The reaction mixture is refluxed overnight and additional hydrazine monohydrate (0.5 g) added and refluxing continued for another 24 hours. The reaction mixture is cooled to RT, filtered, and the filtered solid is dried in vacuo, affording the desired product, M.P.>250° C.

EXAMPLE 4

The Preparation of
3,4-Dihydro-6-[3-(4,5-Dihydro-Pyridizin-6-one)]-1-Methyl-2(1H)-Quinazolinone

Step 1.
6-(3-Carbomethoxy-propionyl)-3,4-dihydro-1-methyl-2(1H)-quinazolinone 3,4-Dihydro-1-methyl-2(1H)-quinazolinone (2.5 g) is added to a stirred suspension of anhydrous aluminum chloride (10.48 g) in carbon disulfide (120 ml) under nitrogen. Methyl succinyl chloride (2.3 g) is added dropwise to the stirred suspension, which is refluxed for about 18 hours and cooled to RT. The liquid phase is decanted and the residue treated with ice-cold H₂O and 6N HCl. The aqueous mixture is filtered and the filtered solid air dried, affording the desired product as a solid, M.P. 165°–175° C., which is used in the next step without further purification.

Step 2.
3,4-Dihydro-6-[3-(4,5-dihydro-pyridizin-6-one)]-1-methyl-2(1H)-quinazolinone Hydrazine monohydrate (0.8 g) is added to a stirred mixture of the keto ester obtained in Step 1. above (3.7 g) in absolute ethanol (85 ml). The reaction mixture is refluxed for about 18 hours, cooled to RT, filtered and the filtered solid dried in vacuo. The solid is resuspended in absolute ethanol (60 ml) and a second portion of hydrazine hydrate (0.4 g) added to the suspension, which is refluxed for about 17 hours, cooled and filtered. The filtered solid is dried in vacuo, affording the desired product, M.P.>250° C.

EXAMPLE 5

The Preparation of
3,4-Dihydro-6-[3-(4,5-Dihydro-4-Methyl-Pyridizin-6-one)]-1-Methyl-2(1H)-Quinazolinone

Step 1.
6-(3-Carbomethoxy-2-methyl-propionyl)-3,4-dihydro-1-methyl-2(1H)-quinazolinone 3,4-Dihydro-1-methyl-2(1H)-quinazolinone (2.5 g) is added to a stirred suspension of anhydrous aluminum chloride (10.5 g) in carbon disulfide (120 ml) under nitrogen. 3-Carbomethoxy-2-methyl-propionyl chloride (2.5 g) is added dropwise to the stirred suspension, which is refluxed for about 18 hours and cooled to RT. The liquid phase is decanted and the residue treated with ice/H₂O and 6N HCl (25 ml). The aqueous mixture is extracted with methylene chloride, the organic extract dried, filtered and concentrated in vacuo, affording the desired product as an oil which is used in the next step without further purification.

Step 2.
3,4-Dihydro-6-[3-(4,5-dihydro-pyridizin-6-one)]-2(1H)-quinazolinone

Hydrazine monohydrate (0.9 g) is added to a stirred mixture of the keto ester obtained in Step 1. above (4.2 g) in absolute ethanol (100 ml). The reaction mixture is refluxed for about 20 hours, a second portion of hydrazine hydrate (0.4 g) added, and refluxing continued for an additional 24 hours. The reaction mixture is cooled to RT, filtered, the filtered solid dried in vacuo, affording the desired product as the ¼ hydrate, M.P.>250° C.

EXAMPLE 6

The Preparation of 3,4-Dihydro-6-[3-(4,5-Dihydro-Pyridizin-6-one)]-3-Methyl-2(1H)-Quinazolinone Step 1. 3,4-Dihydro-3-methyl-2(1H)-quinazolinone 1,1'-Carbonyl-diimidazole (16.7 g) is added to a solution of 2-(methylaminomethyl)-aniline (11.2 g) in anhydrous THF (30 ml) under nitrogen. The reaction mixture is refluxed for about 24 hours, stirred for 48 hours at RT and filtered. The filtered precipitate is suspended in 2N HCl for about 40 minutes, filtered, and the filtered solid washed with water and air dried, affording the desired product, M.P. 202°–206.5° C., used in the next step without further purification.

Step 2.
3,4-Dihydro-6-(3-carbomethoxy-propionyl)-3-methyl-2(1H)-quinazolinone 3,4-Dihydro-3-methyl-2(1H)-quinazolinone (10.2 g) is added to a stirred suspension of anhydrous aluminum chloride (42.7 g) and carbon disulfide (250 ml) under nitrogen. Methyl succinyl chloride (9.5 g) is added dropwise to the stirred suspension, which is refluxed for about 24 hours and cooled to RT. The liquid phase is decanted and the residue treated with ice, cold water and cold 6N HCl. The acidic suspension is stirred at RT and filtered, affording the crude product as a tan solid, which is used in the next step without further purification.

Step 3.
3,4-Dihydro-6-[3-(4,5-dihydro-pyridizin-6-one)]-3-methyl-2(1H)-quinazolinone A mixture of hydrazine monohydrate (1.1 g) and the keto ester obtained in Step 2. above (5 g) in absolute ethanol (250 ml) is refluxed for three days. The reaction mixture is cooled to RT, filtered, and the filtered solid suspended in absolute ethanol. A second portion of hydrazine monohydrate (0.5 g) is added to the suspension, which is refluxed for about 24 hours, cooled to RT, filtered and dried, affording the desired product as a quarter hydrate, M.P.>250° C.

EXAMPLE 7

The Preparation of 3,4-Dihydro-6-[3-(4,5-Dihydro-4-Methyl-Pyridizin-6-one)]-3-Methyl-2(1H)-Quinazolinone Step 1.
6-(3-Carbomethoxy-3-methyl-propionyl)-3,4-dihydro-3-methyl-2(1H)-quinazolinone 3,4-Dihydro-3-methyl-2(1H)-quinazolinone (2.5 g) is added to a stirred suspension of anhydrous aluminum chloride (10.5 g) in carbon disulfide (120 ml) under nitrogen. 3-Carbomethoxy-2-methyl-propionyl chloride (2.5 g) is added dropwise to the stirred suspension, which is refluxed for about 18 hours and cooled to RT. The liquid phase is decanted and the residue treated with H₂O (120 ml) and extracted with methylene chloride. The organic extract is dried, filtered and concentrated in vacuo, affording the desired product as a solid, which is used in the next step without further purification.

Step 2.
3,4-Dihydro-6-[3-(4,5-dihydro-4-methyl-pyridizin-6-one)]-3-methyl-2(1H)-quinazolinone Hydrazine monohydrate (0.82 g) is added to a stirred suspension of the keto ester obtained in Step 1. above (4 g) in absolute ethanol (75 ml). The reaction mixture is refluxed for about 20 hours, a second portion of hydrazine hydrate added (0.4 g) and refluxing continued for an additional 24 hours. The reaction mixture is cooled to RT, filtered and dried in vacuo, affording the desired product, M.P.>250° C.

EXAMPLE 8

The Preparation of 3,4-Dihydro-6-[3-(4,5-Dihydro-Pyridizin-6-one)]-2(1H)-4-Methyl-Quinazolinone Step 1.
6-(3-Carbomethoxy-propionyl)-3,4-dihydro-4-methyl-2(1H)-quinazolinone 3,4-Dihydro-4-methyl-2(1H)-quinazolinone (3.7 g) is added to a stirred suspension of anhydrous aluminum chloride (15.3 g) in carbon disulfide (120 ml) under nitrogen. Methyl succinyl chloride (3.4 g) is added dropwise to the stirred suspension, which is refluxed for about 20 hours and cooled to RT. The liquid phase is decanted and the residue treated with ice/H₂O (150 ml), 6N HCl and extracted with methylene chloride. The organic extract is dried, filtered, and concentrated in vacuo, affording the desired crude product as a solid, M.P. 142°–150° C., which is used in the next step without further purification.

Step 2.
3,4-Dihydro-6-[3-(4,5-dihydro-pyridizin-6-one)]-2(1H)-4-methyl-quinazolinone Hydrazine monohydrate (0.8 g) is added to a stirred mixture of the keto ester obtained in Step 1. above (3.7 g) in absolute ethanol (85 ml). The reaction mixture is refluxed for about 17 hours, cooled to RT and filtered. The filtered solid is resuspended in absolute ethanol (75 ml), and additional hydrazine hydrate (0.4 g) added to the suspension, which is refluxed for another 17 hours, cooled, filtered and dried in vacuo, affording the desired product as a solid, M.P.>250° C.

EXAMPLE 9

The Preparation of
3,4-Dihydro-6-[3-(4,5-Dihydro-4-Methyl-Pyridizin-6-one)]-4-Methyl-2(1H)-Quinazolinone

Step 1.
6-(3-Carbomethoxy-2-methyl-propionyl)-3,4-dihydro-4-methyl-2(1H)-quinazolinone 3,4-Dihydro-4-methyl-2(1H)-quinazolinone (3.9 g) is added to a stirred suspension of anhydrous aluminum chloride (16.5 g) in carbon disulfide (120 ml) under nitrogen. 3-Carbomethoxy-2-methyl-propionyl chloride (4 g) is added dropwise to the stirred suspension, which is refluxed for about 17 hours and cooled to RT. The liquid phase is decanted and the residue is treated with ice/H$_2$O (150 ml) and extracted with methylene chloride. The organic extract is dried, filtered, and concentrated in vacuo, affording the desired crude product as an oil, which is used in the next step without further purification.

Step 2.
3,4-Dihydro-6-[3-(4,5-dihydro-4-methyl-pyridizin-6-one)]-4-methyl-2(1H)-quinazolinone Hydrazine monohydrate (0.72 g) is added to a stirred mixture of the keto ester obtained in Step 1. above (3.5 g) in absolute ethanol (85 ml). The reaction mixture is refluxed for about 22 hours, cooled to RT and filtered. The filtered solid is resuspended in absolute ethanol (75 ml), and additional hydrazine hydrate (0.4 g) added to the suspension, which is refluxed for about 18 hours, cooled, filtered and dried in vacuo, affording the desired product as a solid, M.P.>250° C.

EXAMPLE 10

The Preparation of
5-[3-(4,5-Dihydro-4-Methylpyridizin-6-one)]-2-Hydroxybenzimidazole

Step 1.
5-(3-Carboxy-2-methyl-propionyl)-2-hydroxybenzimidazole

Carbon disulfide (90 ml), 2-hydroxybenzimidazole (4.1 g) and 2-methyl-3-carbomethoxy propionyl chloride (5 g) are added to aluminum chloride (20.3 g) under nitrogen. The resulting mixture is refluxed for about 45 hours, quenched with ice cold 6N HCl and the acidic mixture filtered. The filtered solid is washed with water and dried in vacuo, affording the desired product as a solid, M.P. 223° C. (dec).

Step 2.
5-[3-(4,5-Dihydro-4-methylpyridizin-6-one)]-2-hydroxybenzimidazole

Hydrazine monohydrate (0.6 g) is added to a suspension of the keto acid obtained in Step 1. above (2.5 g) in ethanol (55 ml). The reaction mixture is refluxed for 48 hours, cooled, filtered and the filtered solid dried in vacuo, affording the desired product as a white solid, M.P.>350° C.

EXAMPLE 11

The Preparation of
5-[3-(4,5-Dihydro-Pyridizin-6-one)]-2-Hydroxybenzimidazole

Step 1. 5-(3-Carboxypropionyl)-2-hydroxyimidazole

Carbon disulfide (110 ml), 2-hydroxybenzimidazole (5 g) and 3-carbomethoxypropionyl chloride (5.6 g) are added to a flask containing aluminum chloride (25 g) under an atmosphere of nitrogen. The resulting suspension is refluxed for about 20 hours, quenched with ice cold hydrochloric acid (6N), stirred and filtered. The filtered solid is washed with water and dried in a vacuum oven, affording the desired compound as a solid, which is used in the next step without further purification, M.P. 295° C. (dec).

Step 2.
5-[3-(4,5-Dihydro)pyridizin-6-one]-2-hydroxybenzimidazole

Hydrazine monohydrate (1 g) is added to a suspension of the keto acid obtained in Step 1. (4 g) in ethanol (92 ml). The reaction mixture is refluxed for about 60 hours, cooled, filtered and dried, affording a tan solid, M.P. 383°–384° C. (lit. 390° C.).

Tables I through VII list compounds which are also within the scope of the present invention.

TABLE I

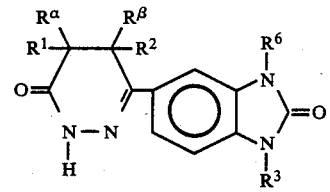

| R$^1$ | R$^\alpha$ | R$^\beta$ | R$^2$ | R$^3$ | R$^6$ |
|---|---|---|---|---|---|
| H | H | H | H | H | H |
| CH$_3$ | H | H | H | H | H |
| H | H | H | CH$_3$ | H | H |
| CH$_3$ | CH$_3$ | H | H | H | H |
| H | H | CH$_3$ | CH$_3$ | H | H |
| CH$_3$ | H | H | H | CH$_3$ | H |
| Et | H | H | H | H | H |
| H | double bond | | H | H | H |
| H | double bond | | CH$_3$ | H | H |

TABLE II

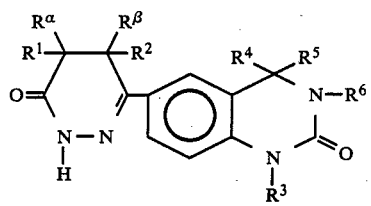

| R¹ | Rα | Rβ | R² | R³ | R⁴ | R⁵ | R⁶ |
|---|---|---|---|---|---|---|---|
| H | H | H | H | H | H | H | H |
| CH₃ | H | H | H | H | H | H | H |
| H | H | H | CH₃ | H | H | H | H |
| H | H | H | H | CH₃ | H | H | H |
| H | H | H | H | H | CH₃ | H | H |
| H | H | H | H | H | H | H | CH₃ |
| CH₃ | H | H | CH₃ | H | H | H | H |
| CH₃ | H | H | H | CH₃ | H | H | H |
| H | H | H | CH₃ | CH₃ | H | H | H |
| CH₃ | H | H | H | H | H | H | CH₃ |
| H | H | H | H | H | CH₃ | CH₃ | H |
| H | H | H | H | H | CH₃ | H | CH₃ |
| CH₃ | H | H | H | H | CH₃ | H | H |
| CH₃ | H | H | H | H | CH₃ | H | CH₃ |
| CH₃ | H | H | CH₃ | H | H | H | CH₃ |
| CH₃ | H | H | CH₃ | H | CH₃ | H | H |
| H | H | H | CH₃ | H | CH₃ | CH₃ | H |
| CH₃ | CH₃ | H | H | H | H | H | H |
| H | H | CH₃ | CH₃ | H | H | H | H |
| CH₃ | CH₃ | H | H | H | H | H | CH₃ |
| Et | H | H | H | H | H | H | H |
| n-C₃H₇ | H | H | H | H | H | H | H |
| H | H | H | n-C₃H₇ | H | H | H | H |
| H | H | H | H | H | Et | H | H |
| H | H | H | H | H | H | H | φCH₂— |
| H | H | H | H | H | H | H | φCH₂CH₂— |
| H | H | H | H | H | φCH₂— | H | H |
| φCH₂— | H | H | H | H | H | H | H |
| CH₃ | H | H | H | H | H | H | φCH₂— |
| H | double bond | H | H | H | H | H | H |
| H | double bond | CH₃ | H | H | H | H | H |
| H | double bond | H | H | H | H | H | CH₃ |
| H | double bond | H | H | CH₃ | H | H | H |
| H | double bond | H | H | CH₃ | H | H | CH₃ |
| CH₃ | CH₃ | H | H | H | H | H | H |
| H | H | CH₃ | CH₃ | H | H | H | H |
| H | H | H | H | H | —CH₂CH₂CH₂— | | H |
| H | H | H | H | H | —CH₂CH₂CH₂CH₂— | | H |
| H | double bond | H | H | —CH₂CH₂CH₂CH₂— | | | H |

TABLE III

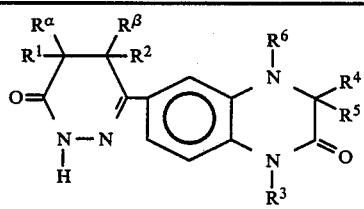

| R¹ | Rα | Rβ | R² | R³ | R⁴ | R⁵ | R⁶ |
|---|---|---|---|---|---|---|---|
| H | H | H | H | H | H | H | H |
| CH₃ | H | H | H | H | H | H | H |
| H | H | H | H | H | CH₃ | H | H |
| H | H | H | H | H | CH₃ | CH₃ | H |
| CH₃ | CH₃ | H | H | H | H | H | H |
| H | H | CH₃ | CH₃ | H | H | H | H |

TABLE III-continued

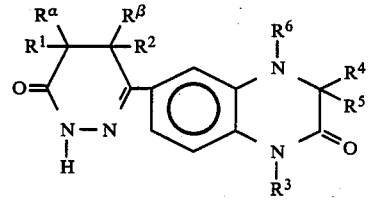

| R¹ | Rα | Rβ | R² | R³ | R⁴ | R⁵ | R⁶ |
|---|---|---|---|---|---|---|---|
| H | H | H | H | CH₃ | H | H | H |
| H | H | H | H | H | CH₂φ | H | H |
| H | double bond | H | H | H | H | H | H |
| H | double bond | H | H | H | CH₃ | CH₃ | H |
| H | double bond | H | H | H | H | H | CH₃ |

TABLE IV

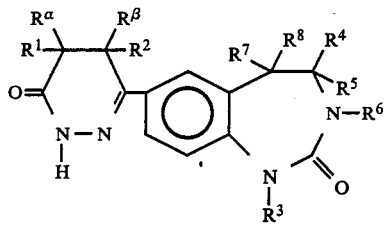

| R¹ | Rα | Rβ | R² | R³ | R⁴ | R⁵ | R⁶ | R⁷ | R⁸ |
|---|---|---|---|---|---|---|---|---|---|
| H | H | H | H | H | H | H | H | H | H |
| H | H | H | H | H | CH₃ | H | H | H | H |
| H | H | H | H | H | H | H | H | CH₃ | H |
| CH₃ | H | H | H | H | H | H | H | H | H |
| H | H | H | H | H | H | H | CH₃ | H | H |
| H | H | H | H | H | H | H | Et | H | H |
| H | H | H | H | H | H | H | φCH₂ | H | H |
| H | H | H | H | H | CH₃ | CH₃ | H | H | H |
| H | H | H | H | H | —CH₂CH₂CH₂CH₂— | | H | H | H |
| H | double bond | | H | H | H | H | H | H | H |
| H | double bond | | H | H | H | CH₃ | H | H | H |

TABLE V

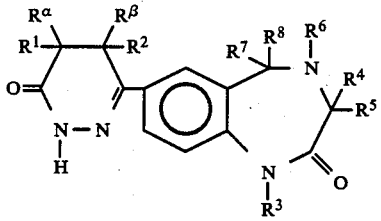

| R¹ | Rα | Rβ | R² | R³ | R⁴ | R⁵ | R⁶ | R⁷ | R⁸ |
|---|---|---|---|---|---|---|---|---|---|
| H | H | H | H | H | H | H | H | H | H |
| H | H | H | CH₃ | H | H | H | H | H | H |
| H | H | H | H | H | H | H | CH₃ | H | H |
| H | double bond | | H | H | H | H | H | H | H |

TABLE VI

| R¹ | Rα | Rβ | R² | R³ | R⁴ | R⁵ | R⁶ | R⁷ | R⁸ |
|---|---|---|---|---|---|---|---|---|---|
| H | H | H | H | H | H | H | H | H | H |
| H | H | H | CH₃ | H | H | H | H | H | H |
| H | H | H | H | H | H | H | CH₃ | H | H |
| H | H | H | H | H | CH₃ | H | H | H | H |
| H | H | H | H | H | CH₃ | H | CH₃ | H | H |
| H | double bond | | H | H | H | H | H | H | H |

TABLE VII

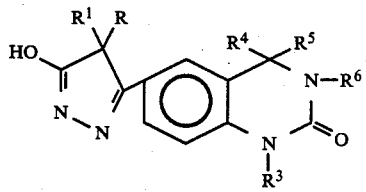

| R¹ | R | R³ | R⁴ | R⁵ | R⁶ |
|---|---|---|---|---|---|
| H | H | H | H | H | H |
| CH₃ | H | H | H | H | H |
| H | H | H | CH₃ | H | H |
| H | H | H | H | H | CH₃ |
| H | H | H | CH₃ | H | CH₃ |
| H | H | H | H | H | φCH₂ |
| CH₃ | H | H | H | H | CH₃ |

The compounds of Formula I possess positive inotropic activity and are useful as cardiotonic agents in the treatment of humans and other mammals for cardiac disorders including congestive heart failure. The effectiveness of the compounds of this invention as inotropic agents may be determined by the following pharmacologic tests which evaluate the change in cardiac contractile force upon exposure to a dose of said compounds. The anesthetized dog procedure is a standard test procedure; the inotropic results of this procedure generally correlate with the inotropic activity found in human patients.

Anesthetized Dog Procedure

Male mongrel dogs are anesthetized with pentobarbital (35 mg/kg i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

The results of the anesthetized dog test show that the compounds of this invention exhibit positive inotropic activity and show dose related increases in contractile force with relatively small increases in heart rate.

Two additional test procedures which have been found to be an efficient means for ascertaining the inotropic activity of the compounds of this invention are described below.

Conscious Instrumented Dog

Female mongrel dogs (18.0–18.5 kg) are anesthetized with sodium pentobarbital (35 mg/kg i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dogs are treated daily post-operatively with 600,000 units of penicillin-procaine i.m. for ten days and with chloramphenicol, 500 mg/kg i.m., every other day for 10 days and allowed at least 7 days recovery before use.

Each dog is trained and acclimated to her environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular end diastolic pressure, left ventricular $dP/dt_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

Guinea Pig Atria Inotropic Screening at Low Calcium Concentrations

Guinea pigs are stunned by a sudden blow to the head; their chests are opened and hearts excised and placed in Kreb's medium (concentrations, μmM: NaCl, 118.39; KCl, 4.70; $MgSO_4$, 1.18; $KH_2PO_4$, 1.18; $NaHCO_3$, 25.00; glucose, 11.66; and $CaCl_2$, 1.25) gassed with a mixture of 95% $O_2$–5% $CO_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is acheived via a pair of platinum or silver electrodes placed on opposite sides of the tissue. Electrodes are made from 20-gauge silver wire wound into a tight coil approximately 12–14 mm in diameter. Electrodes are connected to a Grass stimulator via a Grass constant current unit. Tissues are driven at 90 pulses per minute with a 5 msec duration at current levels 20% greater than threshold for continuous beat.

Cumulative concentrations of test drugs are added to the tissue bath at intervals sufficient to allow developed tension to peak at a new level.

The increase in developed tension in each tissue for each compound concentration is measured, and the results are averaged and used to construct cumulative concentration-response curves. Slopes for these regressions are calculated via the method of Finney (1971) and compared using Student's t-test.

The compounds of this invention can be normally administered orally or parenterally, in the treatment of cardiac disorders such as heart failure in humans or other mammals.

The compounds of this invention may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearte, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, made isotonic with sufficient saline or glucose and sterilized by heating or by microfiltration.

The dosage regimen in carrying out the method of this invention is that which insures maximum therapeutic response until improvement is obtained and thereafter the minimum effective level which gives relief.

Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

We claim:

1. A method for increasing cardiotonic contractility in a human or other mammal requiring such treatment which comprises administering thereto an effective inotropic amount of compound according to the formula

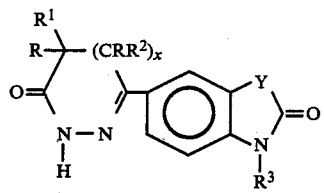

wherein:
x is 0 to 1;
Y is

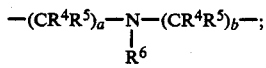

a and b are 0, 1 or 2, provided that a+b is not greater than 2;
$R^1$, $R^2$, $R^3$, $R^4$ and $R^6$ are each independently H, alkyl or aralkyl;
R and $R^5$ are H or alkyl;
R or $R^5$ groups on vicinal carbon atoms may together form a carbon-carbon double bond; and
geminal $R^4$ and $R^5$ groups may together form a spiro substituent, —(CH$_2$)$_d$—, where d is 2 to 5;
or a pharmaceutically acceptable salt thereof.

2. A method according to claim 1 wherein the effective inotropic compound is 5-[3-(4,5-dihydropyridizin-6-one)]-2-hydroxybenzimidazole or a pharmaceutically acceptable salt thereof.

3. A method according to claim 1 which said compound is 3,4-dihydro-6-[5-(3-hydroxy-4-methylpyrazolyl)]-2(1H)-quinazolinone or a pharmaceutically acceptable salt thereof.

4. A method according to claim 1 wherein said compound is 3,4-dihydro-6-[5-(3-hydroxy-pyrazolyl)]-4-methyl-2(1H)-quinazolinone or a pharmaceutically acceptable salt thereof.

5. A compound according to claim 1 which is 3,4-dihydro-6-[5-(3-hydroxy-pyrazolyl)]-3-methyl-2(1H)-quinazolinone or a pharmaceutically acceptable salt thereof.

6. A method according to claim 1 wherein said compound is 3,4-dihydro-6-[5-(3-hydroxy-pyrazolyl)]-3,4-dimethyl-2(1H)-quinazolinone or a pharmaceutically acceptable salt thereof.

7. A method according to claim 1 wherein said compound is 3,4-dihydro-6-[5-(3-hydroxy-pyrazolyl)]-3-benzyl-2(1H)-quinazolinone or a pharmaceutically acceptable salt thereof.

8. A method according to claim 1 wherein said compound is 3,4-dihydro-6-[5-(3-hydroxy-4-methyl-pyrazolyl)]-3-methyl-2(1H)-quinazolinone or a pharmaceutically acceptable salt thereof.

9. A method according to claim 1 wherein said compound is 3,4-dihydro-6-[5-(3-hydroxy-pyrazolyl)]-2(1H)-quinazolinone or a pharmaceutically acceptable salt thereof.

10. A method according to claim 1 wherein said compound is 3,4-dihydro-6-[3-(4,5-dihydro-pyridizin-6-one)]-2(1H)-quinazolinone or a pharmaceutically acceptable salt thereof.

11. A method according to claim 1 wherein said compound is 3,4-dihydro-6-[3-(4,5-dihydro-4-methyl-pyridizin-6-one)]-2(1H)-quinazolinone or a pharmaceutically acceptable salt thereof.

12. A method according to claim 1 wherein said compound is 3,4-dihydro-6-[3-(4,5-dihydro-pyridizin-6-one)]-1-methyl-2(1H)-quinazolinone or a pharmaceutically acceptable salt thereof.

13. A method according to claim 1 wherein said compound is 3,4-dihydro-6-[3-(4,5-dihydro-4-methyl-pyridizin-6-one)]-1-methyl-2(1H)-quinazolinone or a pharmaceutically acceptable salt thereof.

14. A method according to claim 1 wherein said compound is 3,4-dihydro-6-[3-(4,5-dihydro-pyridizin-6-one)]-3-methyl-2(1H)-quinazolinone or a pharmaceutically acceptable salt thereof.

15. A method according to claim 1 wherein said compound is 3,4-dihydro-6-[3-(4,5-dihydro-4-methyl-pyridizin-6-one)]-3-methyl-2(1H)-quinazolinone or a pharmaceutically acceptable salt thereof.

16. A method according to claim 1 wherein said compound is 3,4-dihydro-6-[3-(4,5-dihydro-pyridizin-6-one)]-2(1H)-4-methyl-quinazolinone or a pharmaceutically acceptable salt thereof.

17. A method according to claim 1 wherein said compound is 3,4-dihydro-6-[3-(4,5-dihydro-4-methyl-pyridizin-6-one)]-4-methyl-2(1H)-quinazolinone or a pharmaceutically acceptable salt thereof.

18. A pharmaceutical composition for increasing cardiotonic contractility in a patient requiring such treatment comprising a pharmaceutically acceptable carrier in admixture with a compound described by the formula

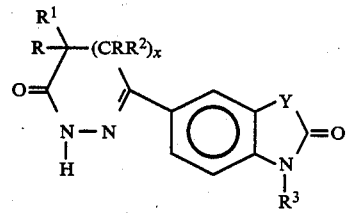

wherein:
x is 0 or 1;
Y is

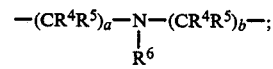

a and b are 0, 1 or 2, provided that a+b is not greater than 2;

$R^1$, $R^2$, $R^3$, $R^4$ and $R^6$ are each independently H, alkyl or aralkyl;

R and $R^5$ are H or alkyl;

R and $R^5$ groups on vicinal carbon atoms may together form a carbon-carbon double bond; and geminal $R^4$ and $R^5$ groups may together form a spiro substituent, $-(CH_2)_d-$, where d is 2 to 5;

or a pharmaceutically acceptable salt thereof.

* * * * *

UNITED STATES PATENT AND TRADEMARK OFFICE
CERTIFICATE OF CORRECTION

PATENT NO. : 4,906,630

DATED : March 6, 1990

INVENTOR(S) : Studt, et al

It is certified that error appears in the above-identified patent and that said Letters Patent is hereby corrected as shown below:

ON THE TITLE PAGE
In the inventorship Item [75], add the following inventors:

Donald E. Kuhla, Doylestown; Henry F. Campbell, Lansdale, both of PA.

Signed and Sealed this

Twenty-eighth Day of May, 1991

Attest:

HARRY F. MANBECK, JR.

Attesting Officer

Commissioner of Patents and Trademarks